United States Patent [19]

Reisner et al.

[11] 4,124,723
[45] * Nov. 7, 1978

[54] METHOD FOR SUPPRESSING HISTAMINE RELEASE

[75] Inventors: David B. Reisner, Hightstown; Bernard J. Ludwig, North Brunswick; George M. Fukui, Princeton, all of N.J.; Frank M. Berger, New York, N.Y.

[73] Assignee: Carter-Wallace, Inc., New York, N.Y.

[*] Notice: The portion of the term of this patent subsequent to Apr. 22, 1992, has been disclaimed.

[21] Appl. No.: 770,062

[22] Filed: Feb. 18, 1977

Related U.S. Application Data

[63] Continuation of Ser. No. 558,063, Mar. 13, 1975, abandoned.

[51] Int. Cl.$^2$ .............................................. A61K 31/22
[52] U.S. Cl. .................................... 424/311; 424/317; 424/337
[58] Field of Search ................ 424/317, 340, 337, 311

[56] References Cited

U.S. PATENT DOCUMENTS

| 3,651,236 | 3/1972 | Kelly et al. | 424/317 |
| 3,879,544 | 4/1975 | Reisner et al. | 424/337 |

OTHER PUBLICATIONS

Chemical Abstracts 67: 90489b (1967).

*Primary Examiner*—Leonard Schenkman
*Attorney, Agent, or Firm*—Kevin B. Clarke

[57] ABSTRACT

A method for suppressing the release of histamine from sensitized leukocytes in warm blooded animals which comprises administering internally to said animals compounds of the formula:

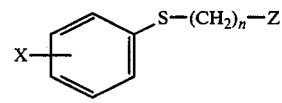

wherein $n$ is a whole integer from 1 to 4; X is halogen and Z is COOH, CH$_2$OR or

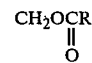

R being a lower alkyl chain of from 1 to 6 carbon atoms and pharmaceutically acceptable salts of those compounds wherein Z is COOH, in sufficient amount to suppress the release of histamine from said cells.

5 Claims, No Drawings

METHOD FOR SUPPRESSING HISTAMINE RELEASE

This application is a continuation of application Ser. No. 558,063 filed Mar. 13, 1975, and now abandoned.

The subject of this invention is a class of compounds chemically described as arylthioalkanoic acids, their pharmaceutically acceptable salts, and ethers and esters of arylthioalkanols which has the ability of suppressing the release of histamine from sensitized leukocytes.

Clinical manifestations of allergic diseases in man are due primarily to the release of histamine from white blood cells which have been sensitized to the agent causing the allergic condition. The released histamine may cause symptoms of allergy such as skin erythema, urticaria, dyspnea, and, in more serious cases, anaphylactic shock. The release of histamine occurs whenever the allergen, i.e., the substance to which the subject is hypersensitive, comes in contact with the sensitized white cells (leukocytes). When this happens, histamine is discharged from these cells and causes the above-mentioned symptoms.

Until recently only antihistamines were available to allay the symptoms of allergy. Antihistamines do not prevent the discharge of histamine from the sensitized cells. All they do is to decrease the sensitivity of some body cells to the effects of histamine. The substances of our invention have no antihistaminic action. They do not decrease the sensitivity of the receptor cells to the effect of histamine. They act in a novel manner by preventing the discharge of histamine from sensitized cells which occurs when these cells come into contact with their specific allergen.

The compounds of the invention can be represented by the following structural formula:

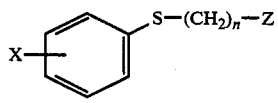

wherein X is halogen; $n$ is a whole integer from 1 to 4; Z is COOH, CH$_2$OR or

where R is lower alkyl, and pharmaceutically acceptable salts of those compounds where Z is COOH. As used throughout the instant specification and claims the term "lower alkyl" shall mean carbon chains containing 1–6 carbon atoms.

The arylthioalkanoic acids, arylthioalkanol ethers and esters which are utilized in the present invention can be conveniently prepared by alkylation of the appropriate thiophenol with a suitable halogenated alkanoic acid or the selected ether or ester of the appropriate halohydrin. Examples I to IV illustate the preparation of representative compounds of this invention.

EXAMPLE I 2-(p-Chlorophenylthio)acetic acid (Compound 2)

This compound was prepared by the method of W. J. Kenney, J. A. Walsh and D. A. Davenport, J. AM. CHEM. SOC., 83: 4020, 1961.

EXAMPLE II

Sodium 4-(p-Chlorophenylthio)butyrate (Compound 1)

4-(p-chlorophenylthio)butyric acid (see G. Kresze, W. Schramm and G. Cleve, BERICHTE, 94:2069, 1961) was prepared as in Example I, m.p. 107°–108°.

A hot solution of 13.8 g of 4-(p-chlorophenylthio)-butyric acid was added to a hot solution of 3.2 g of sodium methoxide in 50 ml of isopropanol. The resulting mixture was cooled and filtered. The air-dried solid weighed 14.4 g.

Anal Calcd for C$_{10}$H$_{10}$ClO$_2$SNa: C, 47.52; H, 3.99; Cl, 14.03; S, 12.69. Found: C, 47.25; H, 4.06; Cl, 13.82; S, 12.66.

EXAMPLE III

Preparation of 4-(p-Chlorophenylthio)butyl acetate (Compound 3)

A mixture of 144.6 g of p-chlorothiophenol, 150.6 g of 4-chlorobutyl acetate, 80 g of 50% aqueous solution of sodium hydroxide and 750 ml of ethyl alcohol was heated under reflux for 5 hours. The alcohol was distilled off and ether was added to the cool mixture. After washing with dilute sodium hydroxide solution and then water, the ether solution was dried, evaporated to dryness and distilled. The product was collected at 110°–116° and 0.01 mm, N$_D^{25}$ 1.5480.

EXAMPLE IV

Preparation of 4-(p-Chlorophenylthio)butyl methyl ether (Compound 4)

To a mixture of 7.2 g of a 57% oil dispersion of sodium hydride and 125 ml of toluene was added a solution of 36.5 g of 4-(p-chlorophenylthio)butanol in 125 ml of toluene. The mixture was stirred and heated under reflux until the evolution of hydrogen ceased. It was then cooled and 25.6 g of methyl iodide was added with stirring. The resulting mixture was heated under reflux for 2 hours, cooled, washed with three portions of water saturated with sodium chloride, dried over anhydrous sodium sulfate and evaporated to dryness. The residue was distilled at reduced pressure to give 17.1 g of product, b.p. 92°–100° at 0.05 mm, N$_D^{25}$ 1.5524.

Anal Calcd for C$_{11}$H$_{15}$ClOS: 57.24; H, 6.55; Cl, 15.36; S, 13.89. Found: C, 57.34; H, 6.69; Cl, 15.43; S, 13.91.

IN VITRO ACTIVITY

The in vitro activity of the compounds of the invention was determined in the manner described below:

Assay for Inhibition of Histamine Release

The procedure published by L. M. Lichtenstein and A. G. Osler, J. EXPTL. MEDICINE, 120:507–530, 1964, for the determination of histamine from human leukocytes, was used to measure histamine release from sensitized rabbit leukocytes. Forty-five ml of blood, drawn by cardiac puncture from ragweed-sensitized rabbits with a plastic syringe containing 250 units of heparin in 5 ml of physiological saline solution, was used. Measurements were made of the total amount of histamine in the leukocytes, the amount of histamine released with the specific antigen (ragweed), the amount of histamine released spontaneously (cell blanks), and the amount of histamine released in the presence of various concratrations of drugs under test.

Appropriate controls for buffer antigen and drugs were included and an internal histamine standard curve was established with each experiment. Inhibition of histamine release was computed from the amount of histamine released by the ragweed antigen in the presence and absence of the drug, i.e., the difference between the quantity of histamine released spontaneously and the amount released by antigen.

Table I which follows shows the $ED_{50}$ (molar concentration required to give 50% inhibition of histamine release) of some of the compounds of this invention and demonstrates the activity of these compounds relative to that of 3-p-chlorophenoxy-1,2-propanediol (chlorphenesin). The latter compound has been reported to inhibit histamine release from human leukocytes (L. M. Lichtenstein and N. F. Adkinson, J. IMMUNOLOGY, 103:866, 1969).

TABLE 1

| Compound | Relative in vitro Inhibition of Histamine Release | $ED_{50}$ + S.E.M. (Molar) |
|---|---|---|
| Chlorphenesin | 1 | $3.3 \pm 0.54 \times 10^{-4}$ |
| 1 | 55 | $6.0 \pm 2.5 \times 10^{-6}$ |
| 2 | 8 | $4.4 \pm 3.3 \times 10^{-5}$ |
| 3 | 52 | $6.3 \pm 0.4 \times 10^{-6}$ |
| 4 | 12 | $2.8 \pm 1.2 \times 10^{-5}$ |

In order to show that the arylthioalkanols of the present invention inhibit the release of histamine when administered orally to ragweed-sensitized rabbits, the following in vivo experiment was carried out:

Five ml of blood was drawn by cardiac puncture from a ragweed-sensitized rabbit to ascertain the basic histamine content of the blood. The amount of histamine released by the addition of 50 μg of antigen N per ml of the assay system was determined. The rabbit was then treated orally with 100 mg/kg of drug using a catheter. One and 5 hr following administration of drug, 5 ml of blood was withdrawn and assayed for histamine by the spectrofluorometric method described by P. A. Shore, A. Burkhalter and V. H. Cohn, Jr., J. PHARMACOL. and EXPTL. THERAP., 127:182, 1959. The percentage inhibition of histamine release was computed from the amount of histamine released before and at 1 and 5 hr following administration of drug. Compound 1 in Table I gave about 30-40% inhibition of histamine release one hour after drug treatment and about 10-15% inhibition 5 hrs after drug treatment.

The compounds employed in this invention are preferably administered orally in the form of tablets, capsules, or the like. The compounds may also be administered using a suspension of the compound in water or isotonic saline solution or a solution of the compound in a solvent consisting of aqueous propylene glycol or polyethylene glycol. In addition to the active ingredient, the tablet contains conventional fillers, excipients, lubricants, etc. The active compound is generally in an amount from 25 to 95% by weight of the total composition. The compounds may also be administered by insufflation into the bronchial passages.

Numerous modifications and variations of the present invention will be obvious to those skilled in the art in light of the foregoing specification and the invention may be practiced in a manner other than as specifically set forth and still fall within the scope of the appended claims.

What is claimed is:

1. A method for suppressing the release of histamine from sensitized leukocytes in a warm blooded animal in need of such treatment which comprises administering internally to said animal, in an amount sufficient to suppress the release of histamine in said animal, a compound selected from the group consisting of a compound having the formula:

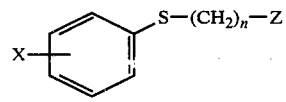

Wherein $n$ is a whole integer from 1 to 4; X is halogen and Z is COOH, $CH_2OR$ or $CH_2OCR$, R being a lower alkyl chain of from 1 to 6 carbon atoms and a pharmaceutically acceptable salt of those compounds wherein Z is COOH.

2. The method according to claim 1 wherein the compound is 4-(p-chlorophenylthio)butyric acid.

3. The method according to claim 1 wherein the compound is 2-(p-chlorophenylthio)acetic acid.

4. The method according to claim 1 wherein the compound is 4-(p-chlorophenylthio)butyl acetate.

5. The method according to claim 1 wherein the compound is 4-(p-chlorophenylthio)butyl methyl ether.

* * * * *